United States Patent [19]

Garcia

[11] 4,000,121

[45] Dec. 28, 1976

[54] PRODUCTION OF ANTISERA COMPRISING FRACTIONATING PLASMA OR SERUM WITH AN ETHYLENE OXIDE-POLYOXYPROPYLENE BLOCK COPOLYMER

[75] Inventor: Luis A. Garcia, Huntington Beach, Calif.

[73] Assignee: Baxter Travenol Laboratories, Inc., Deerfield, Ill.

[22] Filed: Oct. 7, 1974

[21] Appl. No.: 512,561

Related U.S. Application Data

[62] Division of Ser. No. 327,894, Jan. 30, 1973, Pat. No. 3,880,989.

[52] U.S. Cl. .............................. 260/112 B; 424/11; 424/12; 424/85; 424/101; 210/53

[51] Int. Cl.² ................. A61K 37/02; A61K 37/06; C07G 7/00

[58] Field of Search ................................. 260/112 B

[56] References Cited

UNITED STATES PATENTS

| | | | |
|---|---|---|---|
| 3,415,804 | 12/1968 | Polson | 260/112 B |
| 3,770,631 | 11/1973 | Fekete et al. | 210/53 |
| 3,850,903 | 11/1974 | Garcia et al. | 260/112 B |

*Primary Examiner*—Howard E. Schain
*Attorney, Agent, or Firm*—Paul C. Flattery; Lawrence W. Flynn; Max D. Hensley

[57] ABSTRACT

A process for the preparation of a stable and concentrated antiserum comprising sequentially fractionating blood plasma or serum with block copolymers of ethylene oxide and polyoxypropylene polymer at selected concentrations and pH's.

5 Claims, No Drawings

PRODUCTION OF ANTISERA COMPRISING FRACTIONATING PLASMA OR SERUM WITH AN ETHYLENE OXIDE-POLYOXYPROPYLENE BLOCK COPOLYMER

This is a division of application Ser. No. 327,894, filed Jan. 30, 1973, now U.S. Pat. No. 3,880,989.

This invention relates to a method for the production of antisera. More particularly, the invention relates to the preparation of stable and concentrated antisera by fractional precipitation of blood serum or plasma.

Mammalian antisera to the most diversified antigens are widely used as immunochemical tools in industry, clinical laboratories and hospitals throughout the world.

Blood grouping and typing sera are among these widely used antisera. They are generally produced by rabbit or other animal immunixation, trial bleedings, assay of raw materials and subsequent preparation of a suitable pool of product through blending to any desired specification.

Concentration of the antibody fraction of such sera is then commonly carried out such as by $(NH_4)_2 SO_4$ and/or "Rivanol" (6,9-diamino-2-ethoxyacridine lactate monohydrate) precipitation.

In accordance with the present invention, an improved method for the preparation of a stable and concentrated antiserum is provided. Normal human or animal plasma or serum, or plasma or serum from immunized humans or animals is fractionated into two major fractions. One fraction consists of high molecular weight proteins including the antibodies, and the other fraction comprises albumin and the lower molecular weight globulins. By further treatment, the high molecular weight fraction is delipidated and reprecipitated to render a highly concentrated antibody paste. The lower molecular weight fraction is further treated to yield a stable protein solution consisting of primarily albumin and α- and β-globulins of lower molecular weight, which can be used as a diluent for antibodies and other biological material, for priming heart-lung apparatus and as an organ perfusate.

Each of the foregoing two major fractions can be used as such, but preferably a blended material is made in which the antibody paste is reconstituted with the above-prepared lower molecular weight protein solution to about ¼ to 1/5 the original volume of the starting material. The antisera thus prepared has a 1- to 4-fold greater antibody potency than in the starting material. It is free of particulate matter and remains clear upon storage at temperatures ranging from 5° to 40° C. The method of the present invention is thereby especially useful for the production of high titer group typing sera.

In the method of the invention, the starting material is subjected to selective precipitation at appropriate pH levels with certain block copolymers which are ethylene oxide-propylene glycol condensation products.

The ethylene oxide-propylene glycol condensation products employed in this invention can be prepared by condensing ethylene oxide with polyoxypropylene polymer. A further description of the preparation of these block copolymers is found in U.S. Patent 2,674,619. These block copolymers can be represented by the following structural formula:

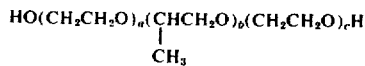

For purposes of this invention, these block copolymers desirably contain at least 50% ethylene oxide in the molecule and a polyoxypropylene hydrophobic base molecular weight of at least 950. Materials containing less than 50% ethylene oxide are not sufficiently non-toxic and products having a hydrophobic base molecular weight less than 950 do not have the desired solubility characteristics. In this respect, the block copolymers employed in this invention are related to and include materials used as blood plasma substitutes and for priming heart-lung apparatus as described in U.S. Pat. Nos. 3,450,502, 3,577,522 and 3,590,125, which are incorporated herein by reference.

Illustrative examples of suitable block copolymers are the F-38 and F-68 "PLURONIC" polyols sold by Wyandotte Chemicals Corp. F-38 contains 80% of polyoxyethylene hydrophilic units in the molecule and the polyoxypropylene hydrophobic base has a molecular weight of 950. F-68 also contains 80% of polyoxyethylene hydrophilic units in the molecule but the hydrophobic base has a molecular weight of 1750. The total molecular weight of these two "PLURONIC" polyols is 4750 and 8750, respectively. A further description of these polyols is found in the bulletin of Wyandotte Chemicals Corp. "The Pluronic Grid", Sixth Edition, which is incorporated herein by reference.

The selective precipitation of the present invention is carried out by the following sequence of steps:

The starting plasma or serum is diluted with water or other aqueous media to a protein concentration of from about 0.5% to about 2.5%. The diluted material is adjusted to a pH of from about 7 to about 8 and thoroughly mixed with the block copolymer to a concentration of from about 12% to about 16%. The resulting precipitate consists of high molecular weight proteins including the antibodies, and the supernatant comprises albumin and the lower molecular weight globulins.

The high molecular weight fraction (precipitate) is separated from the supernatant and diluted with saline or other aqueous media to a protein concentration of from about 0.5% to about 2.5%. The diluted material is adjusted to a pH of from about 4.5 to about 5.5 and thoroughly mixed with the block copolymer to a concentration of from about 4.5% to about 5.5%. The resulting precipitate is separated from the supernatant and discarded. The supernatant, which contains the immune globulins, is adjusted to a pH of from about 6 to 8 and thoroughly mixed with the block copolymer to a concentration of from about 14% to about 18%. The resulting precipitate (antibody paste) is collected and retained as the desired high molecular weight protein fraction and the supernatant is discarded.

The above-prepared lower molecular weight fraction (supernatant) which was initially separated from the high molecular weight fraction is adjusted to a pH of from about 7 to about 8 and thoroughly mixed with the block copolymer to a concentration of from about 20% to about 24%. The resulting precipitate is separated from the supernatant and discarded. The supernatant, which contains albumin and the α- and β-globulins, is buffered at a pH of from about 4 to about 5 with thorough mixing while the block copolymer is held at a concentration of from about 20% to about 24%. In this step, the NaCl concentration preferably is brought to a molarity of 0.15. The resulting precipitate is then collected as the desired lower molecular weight protein fraction and the supernatant is discarded.

The above-prepared lower molecular weight protein fraction preferably is placed in solution form. This is achieved by diluting with water or other aqueous media to a concentration of from about 2% to about 4% protein, adjusting the pH to a level of from about 6.5 to about 7.5 and adjusting the electrolyte concentration to a level of from about 135 to about 155 milliequivalents of sodium per liter.

The thus-reconstituted lower molecular weight fraction preferably is clarified by treatment with a diatomaceous earth such as "Celite" and sterile filtered by passage through a "Millipore" filter using 0.22 micron pads.

Preferably, the antibody paste is then reconstituted by admixing with the thus-prepared lower molecular weight protein solution to about ¼ to 1/5 the volume of the original starting material. This reconstituted material then also preferably is clarified and filtered as was done above for the lower molecular weight protein solution.

The following examples will further illustrate the invention although the invention is not limited to these specific examples.

EXAMPLE 1 a. Normal human blood plasma is diluted with distilled water to a protein concentration of 1.5 gram percent (grams/100 ml.) and the pH is adjusted to 7.5. "PLURONIC" F-38 is added to the diluted plasma to a concentration of 14 gm. % and mixed for 1–2 hours at 10°– 30° C. The resulting suspension is centrifuged and then both the precipitate and supernatant are collected. The supernatant is retained for further treatment in part (c), below.

b. The collected precipitate is suspended in normal physiological saline (0.85% NaCl) to a protein concentration of 1.5 gm. % and the pH is adjusted to 5. "PLURONIC" F-38 is added to the diluted precipitate to a concentration of 5 gm. % and mixed for 1–2 hours at 10° – 30° C. The resulting suspension is centrifuged, the precipitate is discarded and the supernatant is adjusted to a pH of 7. "PLURONIC" F-38 is added to the retained supernatant to a concentration of 16 gm. % and mixed for 1–2 hours at 10° – 30° C. The resulting suspension is centrifuged, the precipitate (antibody paste) is collected and retained as the desired high molecular weight protein fraction while the supernatant is discarded.

c. The supernatant retained from part (a), above, is adjusted to a pH of 7.5. "PLURONIC" F-38 is added to a concentration of 22 gm. % and mixed for 1–2 hours at 10° – 30° C. The resulting suspension is centrifuged and the precipitate is discarded. The pH of the retained supernatant is buffered to 4.5 with a mixture of 0.8 molar sodium acetate and 4 normal acetic acid, the sodium chloride concentration is adjusted to 0.15 molarity, and "PLURONIC" F-38 is held at a concentration of 22 gm. % while mixing for 1–2 hours at 10° – 30° C. The resulting suspension is centrifuged, the precipitate is collected and retained as the desired lower molecular weight protein fraction while the supernatant is discarded.

d. The final precipitate retained from part (c), above, is dissolved in distilled water to a protein concentration of 3 gm. %. The pH of the solution is adjusted to 7 with normal sodium hydroxide and the electrolyte concentration adjusted to 145 milliequivalents of sodium per liter. The solution is then filtered through asbestos pads and sterile filtered to 0.22 micron.

e. The high molecular weight protein fraction (antibody paste) retained from part (b), above, is then mixed with sufficient solution of the lower molecular weight protein retained from part (d), above, to ¼ to 1/5 the original volume of the plasma starting material in part (a), above. The solution is clarified with "Celite" diatomaceous earth, cooled to 4° C and sterile filtered to 0.22 micron.

The final blended antisera from several runs made according to the above example using various plasma and serum starting materials were assayed and found to have the following characteristics:

1. The immunoelectrophoretic pattern resembled that of the starting materials except that the immune serum globulin precipitant lines were sharper in the fractionated product.

2. The radial immunodiffusion determination showed that the fractionated product has a 3- to 4- fold greater content of IgG and IgAl immunoglobulin content than that of the starting material.

3. Samples of the blended antisera made from group typing sera according to Example 1 were shown to have a 2- to 4- fold increase in both the saline and the Coombs isoagglutinin titers.

4. At least 80% of the total IgG and at least 70% of the total IgM available in the starting material was retained in the final blended antisera.

5. The product was free of particulate matter upon storage at 5° C and 24° C for four months and no visible particulate matter was observed when agitated four hours on a mechanical shaker.

EXAMPLE 2

The procedure of Example 1 is repeated except that "PLURONIC" F-68 is substituted for an equivalent amount of the "PLURONIC" F-38 with substantially similar results.

Various other examples and modifications of the foregoing examples will be apparent to those skilled in the art after reading the foregoing disclosure. All such further examples and modifications as come within the spirit and scope of the invention are included in the appended claims.

What is claimed is:

1. A process for obtaining immuno globulins from blood plasma or serum by fractionation with a copolymer of the formula

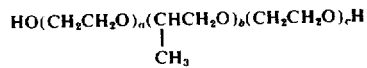

wherein $a$ and $c$ are integers such that the hydrophile portion represented by ($CH_2CH_2O$) constitutes at least about 50% of the molecule and $b$ is an integer such that the hydrophobic portion represented by

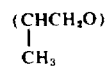

has a molecular weight of at least about 950 comprising admixing said plasma or serum with from about 12% to about 16% by weight of the copolymer at a pH of from about 7 to about 8, collecting the precipitate from the resulting suspension and diluting said precipitate with an aqueous media to a protein concentration of from about 0.5% to about 2.5% and admixing with from about 4.5% to about 5.5% by weight of the copolymer at a pH of from about 4.5 to about 5.5, and separating the supernatant from the resulting suspension.

2. The process of claim 1 in which the block copolymer contains about 80% of polyoxyethylene hydrophilic units in the molecule and the polyoxypropylene hydrophobic base has a molecular weight of about 950.

3. A process for the preparation of a stable diluent for biological materials from blood plasma or serum by fractionation with a copolymer of the formula

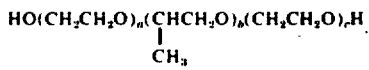

wherein $a$ and $c$ are integers such that the hydrophile portion represented by $(CH_2CH_2O)$ constitutes at least about 50% of the molecule and $b$ is an integer such that the hydrophobic portion represented by

has a molecular weight of at least about 950, comprising diluting said plasma or serum to a protein concentration of from about 0.5% to 2.5%, admixing said diluted plasma or serum with from about 12% to about 16% by weight of the copolymer at a pH of from about 7 to about 8, separating the supernatant from the resulting suspension and admixing with from about 20% to about 24% by weight of the copolymer at a pH of from about 7 to about 8, separating the supernatant from the resulting suspension, admixing with buffer at a pH of from about 4 to about 5 while holding the copolymer concentration at about 20% to about 24% and collecting the resulting precipitate.

4. The process of claim 3 in which the block copolymer contains about 80% of polyoxyethylene hydrophilic units in the molecule and the polyoxypropylene hydrophobic base has a molecular weight of about 950.

5. A process according to claim 1 wherein the supernatant from the last step is admixed with from about 14% to about 18% of the copolymer at a pH from about 6 to about 8 and the resulting precipitate is collected.

* * * * *

UNITED STATES PATENT AND TRADEMARK OFFICE
CERTIFICATE OF CORRECTION

PATENT NO. : 4,000,121
DATED : December 28, 1976
INVENTOR(S) : Luis A. Garcia

It is certified that error appears in the above-identified patent and that said Letters Patent are hereby corrected as shown below:

Column 2, line 54, delete "immune" and insert therefor -- immuno --;

Column 4, line 26, delete "IgAl" and insert therefor --IgM--.

Signed and Sealed this

Fourteenth Day of June 1977

[SEAL]

Attest:

RUTH C. MASON
*Attesting Officer*

C. MARSHALL DANN
*Commissioner of Patents and Trademarks*